US00PP36533P3

(12) United States Plant Patent
Williams

(10) Patent No.: US PP36,533 P3
(45) Date of Patent: Mar. 4, 2025

(54) ***COLOCASIA* PLANT NAMED 'COPHANTO'**

(50) Latin Name: ***Colocasia* hybrid**
Varietal Denomination: COPHANTO

(71) Applicant: Brian's Botanicals, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 16 days.

(21) Appl. No.: 18/445,951

(22) Filed: Apr. 11, 2024

(65) Prior Publication Data

US 2024/0349632 P1 Oct. 17, 2024

(30) Foreign Application Priority Data

Apr. 12, 2023 (QZ) ..... PBR 2023/0849

(51) Int. Cl.
*A01H 5/12* (2018.01)
*A01H 6/10* (2018.01)
*A01H 6/12* (2018.01)

(52) U.S. Cl.
USPC ..... Plt./373
CPC ..... *A01H 6/10* (2018.05); *A01H 6/12* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

'COPHANTO' is a new and distinctive *Colocasia* plant which is characterized by near-black, strongly rugose, and velvety laminas borne on near-black petioles, heavily glaucous foliage which has an iridescent quality when viewed in direct sunlight, and the stability of all characteristics from generation to generation.

3 Drawing Sheets

Latin name of the genus and species: The Latin name of the genus and species of the novel variety disclosed herein is *Colocasia* hybrid.

Variety denomination: The inventive variety of *Colocasia* disclosed herein has been given the variety denomination 'COPHANTO'.

CROSS-REFERENCE TO RELATED APPLICATIONS

This application claims priority to European Community Plant Variety Office (CPVO) Plant Breeder's Rights Application No. 2023/0849 filed on Apr. 12, 2023, under 35 U.S.C. 119(f), the entire contents of which is incorporated by reference herein. The Applicant, Brian's Botanicals, received the information for the Plant Breeder's Rights application directly from the Inventor.

BACKGROUND OF THE INVENTION

Parentage: The claimed plant originated as a seedling selection, resulting from the controlled pollination of the proprietary seed parent, *Colocasia* sp. 'Hybrid Cranberry 2017' (not patented), and the proprietary pollen parent, *Colocasia* sp. 'Hybrid Black Waves 2016' (not patented). Both parents were developed and owned by the inventor and were never commercially released. The cross was performed by the inventor at a commercial greenhouse in Louisville, Kentucky on Aug. 12, 2014. Seeds from said cross were harvested, then germinated, and the resulting seedlings were grown to a mature size in order to evaluate for desirable commercial characteristics. In June of 2021, the inventor selected the claimed *Colocasia* plant for commercialization due to its near-black, velvety, and strongly rugose foliage.

Asexual Reproduction: Asexual reproduction of 'COPHANTO' by way of tuber division, and later by way of meristematic tissue culture propagation, was first performed in June of 2021 at a commercial greenhouse in Louisville, Kentucky. Approximately five hundred plants so produced have shown that the unique features of the instant cultivar are stable and reproduced true to type.

SUMMARY OF THE INVENTION

The cultivar 'COPHANTO' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Colocasia* cultivar 'COPHANTO'. These traits, in combination, distinguish 'COPHANTO' as a new and distinct cultivar.

1. *Colocasia* 'COPHANTO' exhibits cordate laminas with a strongly rugose and velvety texture, borne on relatively long petioles that arise directly from the base of the plant; and
2. *Colocasia* 'COPHANTO' exhibits very dark purple petioles which generally appear as near-black in indirect sunlight; and
3. *Colocasia* 'COPHANTO' exhibits foliage with a very dark purple and heavily glaucous adaxial laminar surface which generally appears as a dark graphite to near-black coloration in indirect sunlight; and 4. *Colocasia* 'COPHANTO' exhibits foliage with a very dark purple and heavily glaucous abaxial laminar surface which generally appear as a mid to dark gray coloration in indirect sunlight and lighter gray in direct sunlight; and
5. *Colocasia* 'COPHANTO' exhibits heavily glaucous foliage that, when viewed in direct sunlight, lends an iridescent quality to the laminas.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
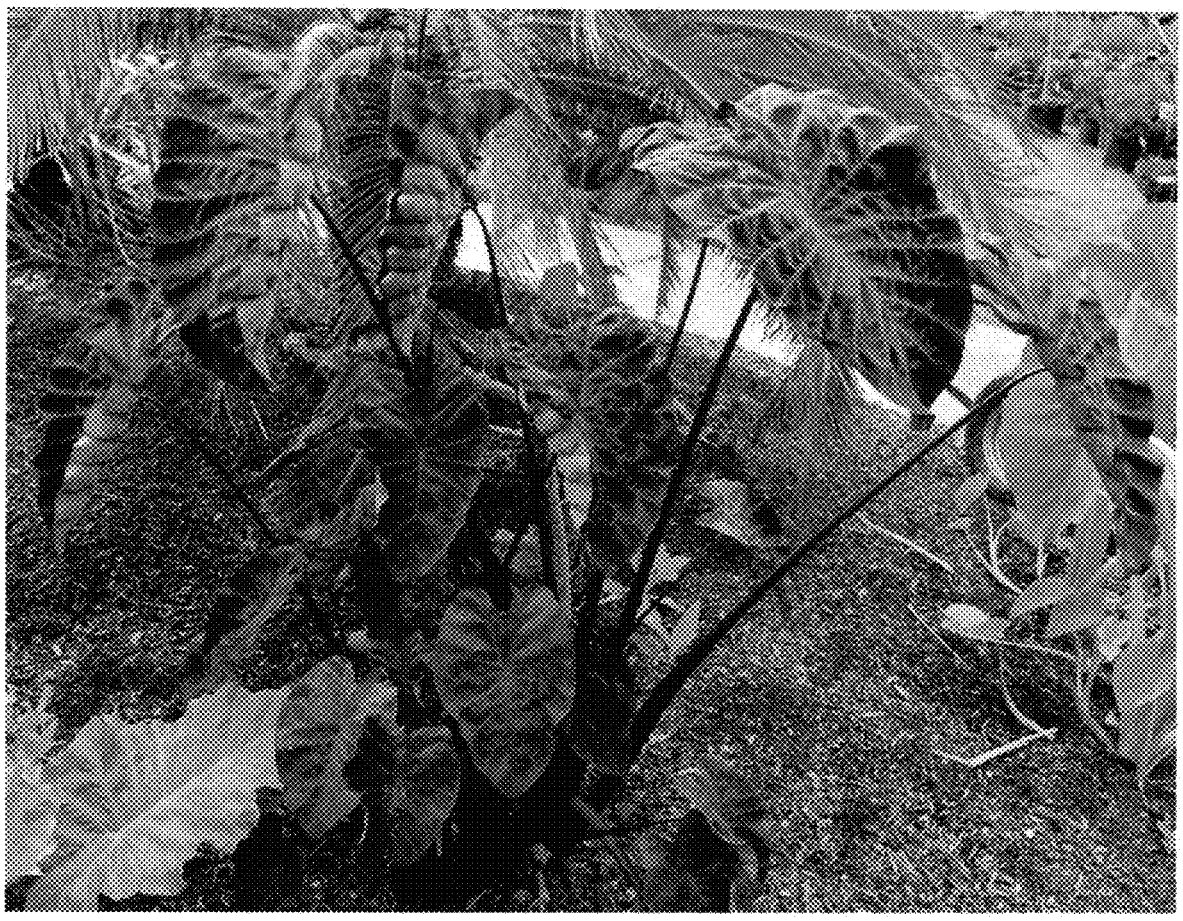
FIG. 1 shows, as nearly true as it is reasonably possible to make the same in color illustrations of this type, an exemplary plant of the new cultivar, 'COPHANTO'. The plant shown is approximately 18 months old, planted outdoors in Louisville, Kentucky.
Figure 2:
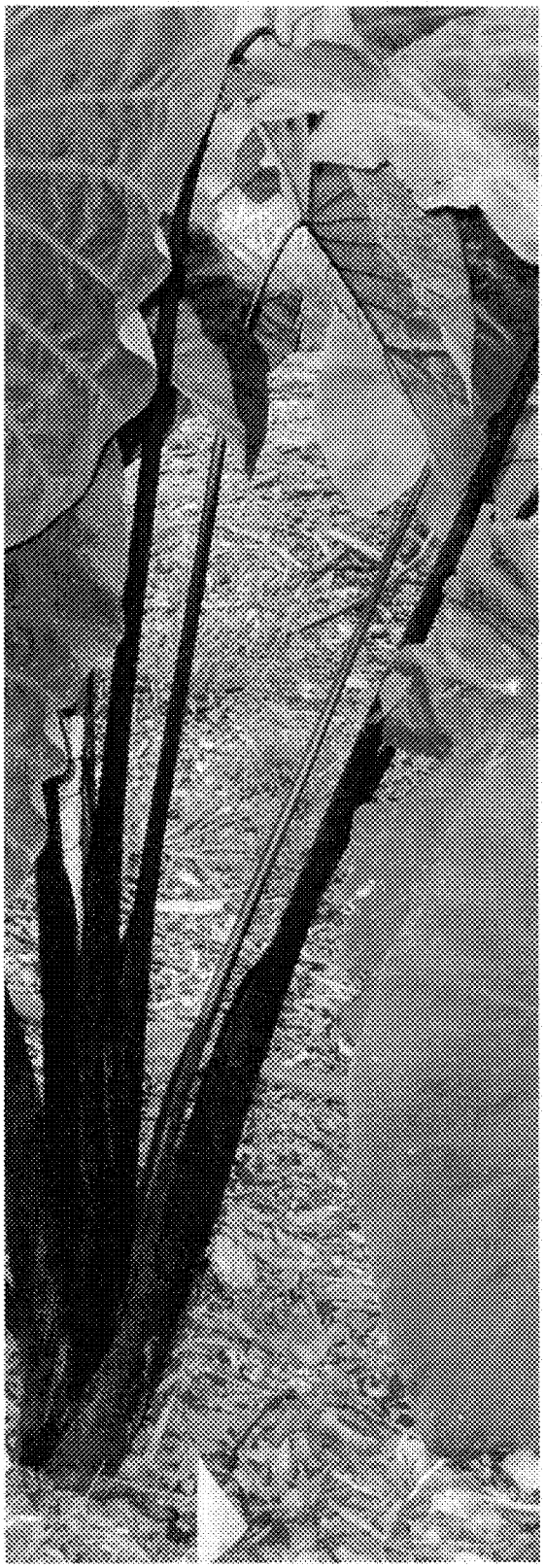
FIG. 2 illustrates the mature petioles of 'COPHANTO'.
Figure 3:
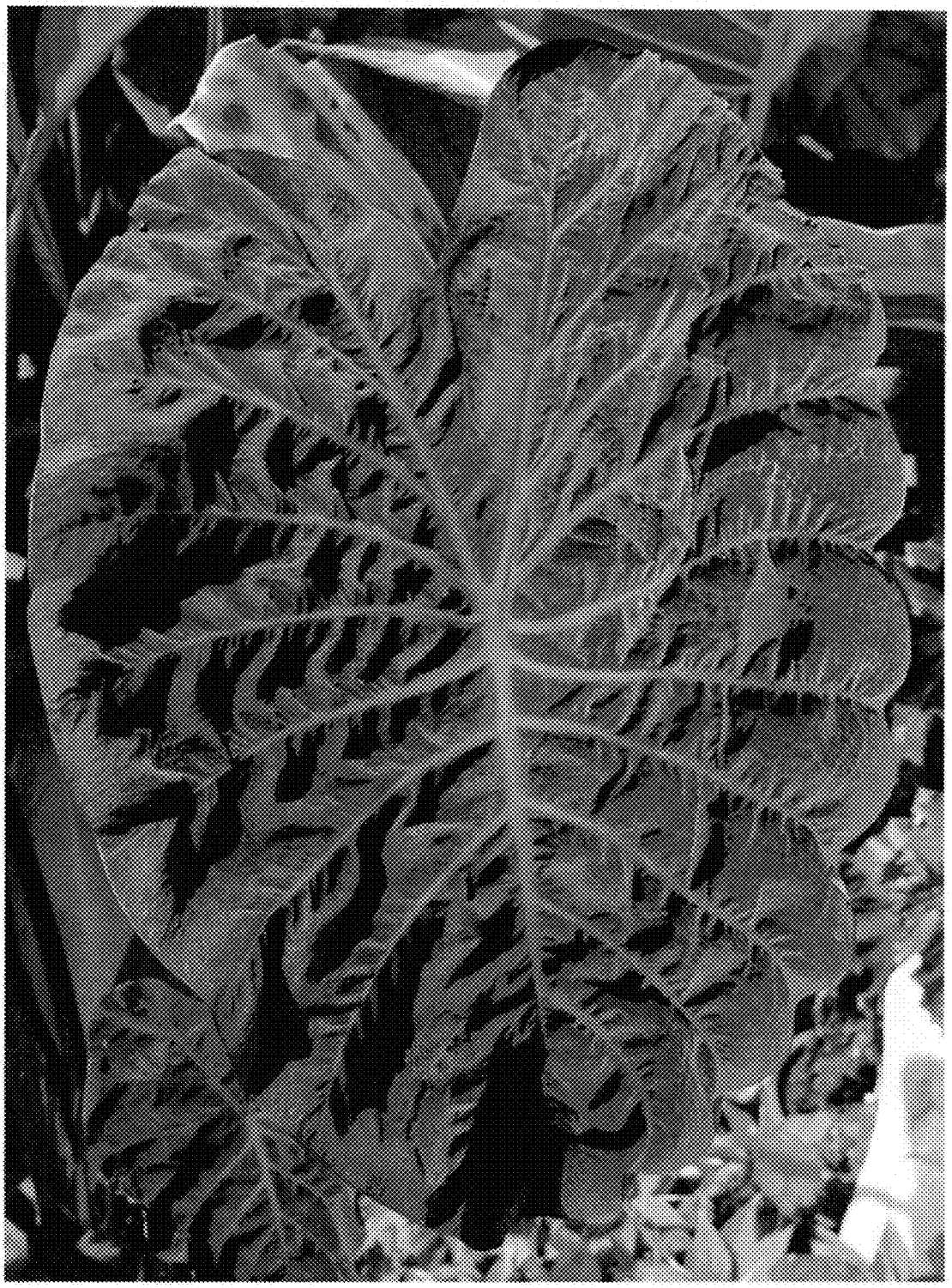
FIG. 3 illustrates the adaxial surface of the mature foliage of 'COPHANTO'.

The following observations and measurements made in October of 2023 describe a 9-month-old 'COPHANTO' plant grown in a 25 cm nursery container at a commercial greenhouse in Louisville, Kentucky. Plants were produced using conventional greenhouse production protocols for *Colocasia* species which consisted of regular overhead irrigation, weekly applications of a liquid 20-20-20 fertilizer at an electroconductivity of 0.8, and anti-bacteria oxalinic acid at a rate of 375 parts-per-million and Imidacloprid insecticide at a rate 100 parts-per-million applied every two weeks. Plants were grown under shade (ranging from 10,000 to 20,000 lux) with ambient temperatures ranging from 20 to 35 degrees Celsius and humidity levels ranging from 70 to 80 percent.

Those skilled in the art will appreciate that certain characteristics will vary with older or, conversely, with younger plants. 'COPHANTO' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, third edition.

A botanical description of 'COPHANTO' and comparisons with the parent plants and the most similar variety of common knowledge are provided below.

General plant description:

*Growth habit*.—Clumping herbaceous perennial; acaulescent, with foliage arising directly from the base of each clump.

*Plant growth habit profile*.—Vase-shaped.

*Height*.—183 cm.

*Width*.—Average 122 cm.

*Growth rate*.—Moderately fast-growing.

*Plant vigor*.—Moderately to highly vigorous.

*Propagation*.—Method — Meristematic tissue culture. Time to initiate roots — Approximately 2 to 5 weeks to initiate roots at an average ambient temperature of 29.4 degrees Celsius. Crop time — Approximately 3 to 5 weeks to produce a well-rooted, marketable 10 cm container from a rooted cutting.

*Environmental tolerances*.—Moderately high tolerance to rain; moderate tolerance to wind; not drought tolerant; tolerant of temperatures to at least 40 degrees Celsius. Cold hardy to USDA Hardiness Zone 8.

*Pest resistance and susceptibility*.—Plants have not been observed to be any more or less susceptible or resistant to pathogens and pests common to *Colocasia* sp.

Root system:

*General*.—Exhibits a shallow root system with fleshy adventitious roots arising from large corms.

*Branching*.—Freely branched.

*Density*.—Moderately dense.

*Distribution*.—Relatively shallow.

*Texture*.—Fleshy; smooth; lacking root hairs.

Stems:

*Branching characteristics*.—Acaulescent; no stems or lateral branches are produced.

Foliage:

*Arrangement*.—Basal foliage is alternate to spiraled.

*Division*.—Simple.

*Attachment*.—Petiolate; peltate.

*Quantity of leaves per shoot*.—12.

*Lamina*.—Shape — Cordate. Apex — Acuminate. Base — Cordate. Aspect — Concave. Attitude — Leaves emerge in the same plane as the petiole yet mature to oblique or pendulous. Dimensions — 61.0 cm long and 46.0 cm wide at maturity. Margin — -Entire; strongly undulated. Texture and luster, adaxial surface — Strongly rugose, glabrous, velvety, matte, and moderately to strongly glaucous. Texture and luster, abaxial surface — Strongly rugose, glabrous, velvety, matte, and moderately to strongly glaucous. Juvenile color, adaxial surface — Nearest to a mixture of green and yellow-green, RHS 137A and 146A, and lightly to moderately suffused with dark purple, nearest to a mixture of RHS 79A and 79B; very narrowly margined greyed-purple, nearest to RHS 187A. Laminas are heavily glaucous which, combined with the dark purple lamina coloration, lends a dark graphite appearance to the foliage when in indirect light and a mid to dark gray iridescent appearance in direct light. Juvenile color, abaxial surface — Nearest to a mixture of green and yellow-green, RHS 137A and 146A, and moderately to strongly suffused with dark purple, nearest to a mixture of RHS 79A and 79B; very narrowly margined greyed-purple, nearest to RHS 187A. Laminas are heavily glaucous which, combined with the dark purple lamina coloration, lends a mid-gray appearance to the foliage when in indirect light and a light gray, iridescent appearance in direct light. Mature color, adaxial surface — Nearest to a mixture of green and yellow-green, RHS 137A and 146A, yet very strongly suffused with dark purple, nearest to a mixture of RHS 79A and 79B yet darker; occasionally further suffused with red-purple, nearest to RHS 59B; very narrowly margined purple, RHS 79A. Laminas are heavily glaucous which, combined with the dark purple lamina coloration, lends a dark graphite appearance to the foliage when in indirect light and a mid to dark gray, iridescent appearance in direct light. Mature color, abaxial surface — Purple, nearest to a mixture of RHS 79A and 79B. Laminas are heavily glaucous which, combined with the dark purple lamina coloration, lends a mid-gray appearance to the foliage when in indirect light and a light gray, iridescent appearance in direct light. Venation — Vein pattern — Pinnate; venation is very prominent and is raised on the abaxial laminar surface. Vein color, adaxial surface — Purple, RHS 79A, and strongly glaucous which lends a greyed appearance. Vein color, abaxial surface — Purple, RHS 79A, and slightly glaucescent.

*Petiole*.—Attachment — Sheathed. Aspect — Terete. Length — Approximately 87 cm. Width — Approximately 2.2 cm, including the petiole wings, at the proximal end and 0.4 cm at the distal end. Strength — Moderately strong. Texture — Smooth and glabrous. Luster — Matte to very slightly glossy. Color, adaxial surface — Very dark purple; in indirect light, the color is nearest to purple, RHS 79A, yet much darker, generally appearing as near-black; in direct light, the color is greyed-purple, nearest to a mixture of RHS 187A and 187B; strongly suffused with greyed-purple 185A near the point of attachment to the lamina. Petiole wings — General Description — Two petiole wings extend to about one-third of the length of the petiole; wings clasped. Length — Approximately 7.6 cm. Width — Approximately 1.25 cm at the base. Margins — Entire. Texture and luster — Glabrous and very slightly glossy. Color — Very dark purple; in indirect light, the color is nearest to purple, RHS 79A, yet much darker; in direct light, the color is greyed-purple, nearest to a mixture of RHS 187A and 187B.

Inflorescence: *Colocasia* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

COMPARISONS WITH THE PARENT

Plants of the new cultivar 'COPHANTO' may be distinguished from the seed parent, *Colocasia* 'Hybrid Cranberry 2017' (not patented), by the characteristics described in Table 1.

TABLE 1

| Characteristic | 'COPHANTO' | 'Hybrid Cranberry 2017' |
|---|---|---|
| General coloration of the mature foliage. | Dark purple and heavily glaucous which lends a dark graphite to near-black coloration to the laminas. | Dark green. |
| Foliage texture. | Strongly rugose and velvety. | Less rugose than 'COPHANTO'. |
| General coloration of the Petiole. | Very dark purple, generally appearing as near-black. | Maroon. |

Plants of the new cultivar 'COPHANTO' may be distinguished from the pollen parent, *Colocasia* 'Hybrid Black Waves 2016' (not patented), by the characteristics described in Table 2.

TABLE 2

| Characteristic | 'COPHANTO' | 'Hybrid Black Waves 2016' |
|---|---|---|
| Plant height. | Taller than 'Hybrid Black Waves 2016'. | Shorter than 'COPHANTO'. |
| Foliage luster. | Matte. | Glossy. |
| General coloration of the mature foliage. | Very dark purple, generally appearing as a dark graphite to near-black coloration. | Gray to near-black. |

COMPARISONS WITH THE MOST SIMILAR COMMERCIAL VARIETY

Plants of the new cultivar 'COPHANTO' may be distinguished from the most similar commercial comparator known to the inventor, *Colocasia* 'Black Magic' (not patented), by the characteristics described in Table 3.

TABLE 3

| Characteristic | 'COPHANTO' | 'Black Magic' |
|---|---|---|
| Plant height. | Taller than 'Black Magic'. | Shorter than 'COPHANTO'. |
| Foliage texture. | Strongly rugose. | Nearly smooth. |

That which is claimed is:

1. A new and distinct variety of *Colocasia* plant named 'COPHANTO', substantially as described and illustrated herein.

* * * * *